United States Patent [19]

Nakamura et al.

[11] 4,224,125
[45] Sep. 23, 1980

[54] ENZYME ELECTRODE

[75] Inventors: Kenichi Nakamura, Hirakata; Shiro Nankai, Neyagawa; Takashi Iijima, Hirakata; Masataro Fukuda, Toyonaka, all of Japan

[73] Assignee: Matsushita Electric Industrial Co., Ltd., Osaka, Japan

[21] Appl. No.: 946,527

[22] Filed: Sep. 26, 1978

[30] Foreign Application Priority Data

Sep. 28, 1977 [JP] Japan ............................ 52/117069

[51] Int. Cl.² ............................................. G01N 31/14
[52] U.S. Cl. ................................. 204/195 B; 204/1 T; 204/195 P; 435/4; 435/817
[58] Field of Search ................ 204/1 E, 195 B, 195 P; 195/103.5 R, 103.5 C, 127, DIG. 11; 429/2; 435/4, 817

[56] References Cited

U.S. PATENT DOCUMENTS

| | | | |
|---|---|---|---|
| 3,539,455 | 11/1970 | Clark | 204/1 T |
| 3,542,662 | 11/1970 | Hicks et al. | 204/195 |
| 3,770,607 | 11/1973 | Williams | 204/195 P |
| 3,788,950 | 1/1974 | Hicks et al. | 195/103.5 R |
| 3,838,033 | 9/1974 | Mindt et al. | 204/195 B |
| 3,948,745 | 4/1976 | Guilbault et al. | 204/195 B |
| 4,073,713 | 2/1978 | Newman | 204/195 B |
| 4,085,009 | 4/1978 | Pace | 204/1 T |
| 4,100,029 | 7/1978 | Prosperi et al. | 195/DIG. 11 X |

FOREIGN PATENT DOCUMENTS 1959169  6/1970  Fed. Rep. of Germany ... 195/DIG. 11

OTHER PUBLICATIONS

G. P. Hicks et al., Anal. Chem., vol. 38, No. 6, pp. 726-730, May 1966.

Primary Examiner—G. L. Kaplan
Attorney, Agent, or Firm—Wenderoth, Lind & Ponack

[57] ABSTRACT

An enzyme electrode, which comprises an oxidoreductase including, where necessary, a coenzyme; a redox polymer acting as an electron mediator in an enzymatic reaction; and an electron collector, wherein the oxidoreductase and the redox polymer are both maintained in the immobilized state on or in the neighborhood of the electron collector by either one of the methods of; entrapping them with a semi-permeable membrane in the neighborhood of the electron collector, or chemically superimposing them on the electron collector or moulding them including the electron collector in a unit with the help of chemical treatment.

10 Claims, 6 Drawing Figures

ENZYME ELECTRODE

BACKGROUND OF THE INVENTION

This invention relates to an enzyme electrode and, more particularly to an enzyme electrode which is utilized for electrochemically measuring concentrations of various substrates which are to be affected by specific catalytic reactions caused by enzymes.

Furthermore, the electrode of the present invention is utilized to convert the chemical energy associated with the substrates mentioned above into electrical energy when assembled into the electrochemical cell with a counter electrode of such as an oxygen electrode.

As is well known, the energy conversion phenomena taking place inside a living organism are mainly controlled by the contributions caused by oxidoreductase, and recently, the phenomena or alternatively, the enzymatic reactions of this kind have been attempted to be utilized in the technological field.

A number of arts related to the enzyme electrode, which can be utilized for measuring the concentration of the substrate in combination with the electrochemical measuring system, have been already proposed.

Before the detailed description of the present invention proceeds, some specific aspects concerning the relation between the oxidation and reduction reaction to be catalyzed by oxidoreductase and the electrochemical measuring system are described in the following.

Generally, without the presence of an electron mediator, the oxidation and reduction reaction of the substrate catalyzed by oxidoreductase can not take place.

When the oxidation of glucose, for example, is to be taken place in the presence of glucose oxidase (GOX), oxygen $O_2$ takes a part of the electron mediator, more particularly functioning as an electron acceptor as shown by the following reaction formula (1).

$$\text{Glucose} + O_2 \xrightarrow{GOX} \text{Gluconolactone} + H_2O_2 \quad (1)$$

More specifically, glucose is oxidized (dehydrogenated) to gluconolactone through the catalytic reaction caused by GOX mentioned above, while, at the same time, oxygen $O_2$ which accepts electrons departed from glucose (electrons associated with hydrogen) is reduced to $H_2O_2$.

In connection with the chemical process mentioned above, the respective concentrations of $O_2$ as well as $H_2O_2$ can be measured with the conventional electrochemical measuring method, thereby it being possible to obtain the concentration of glucose indirectly by means of the direct electrochemical measurements of $O_2$ consumption as well as $H_2O_2$ formation governed by the reaction formula (1) mentioned above.

As far as GOX is employed as an enzyme for the enzymatic reaction, instead of the natural electron acceptor $O_2$ mentioned above, one of the following artificial electron acceptors such as p-benzoquinone, methyleneblue, 2,6-dichloropholindophenol, potassium ferricyanide etc., which are often called by the name of redox compound, can be applied.

More specifically, when p-benzoquinone, for example, is introduced in place of $O_2$ in the chemical process governed by the reaction formula (1) mentioned in the foregoing, a reaction governed by the following reaction formula (2) is to take place.

$$\text{Glucose} + \text{p-benzoquinone} \xrightarrow{GOX} \text{Gluconolactone} + \text{Hydroquinone} \quad (2)$$

In connection with the chemical process mentioned above, since p-benzoquinone as well as hydroquinone are both electrochemically active materials, the respective concentrations of these can be directly measured and thereby, the concentration of glucose can be also indirectly measured with the governing chemical formula.

Furthermore, in addition to GOX, such oxidoreductases as xanthine oxidase, amino acid oxidase, and aldehyde oxidase etc. can accomplish the oxidation and reduction reaction concerning the substrate with one of the artificial electron acceptors defined as the redox compound mentioned in the foregoing in place of the natural electron acceptor such as $O_2$ through the catalytic reaction thereof.

However, depending upon the nature of the oxidoreductases, some oxidoreductases need the presence of one of the compound-group termed by a coenzyme as the electron mediator to accomplish the oxidation and reduction reaction of the substrate concerned.

For example, such oxidoreductase as alcohol dehydrogenase or lactate dehydrogenase needs nicotinamide adenine dinucleotide (NAD) as the coenzyme for the respective reactions.

In addition to NAD mentioned above, nicotinamide adenine dinucleotide phosphate as well as lipoic acid are both known as the coenzyme, while NAD is a typical coenzyme.

In the circumstances where the enzymatic reaction concerning oxidation or reduction of substrates needs a coenzyme as the electron mediator, it is not practically possible to replace the coenzyme with one of the artificial redox compounds.

However, if the coenzyme is involved in the catalytic reaction in the presence of the redox compound, the substrate concentration of the chemical system becomes measurable through the electro-chemical measurement of the redox compound.

For example, when lactate dehydrogenase, NAD, and phenazine methosulfate are employed as the enzyme, the coenzyme, and the redox compound respectively, lactic acid undergoes dehydrogenation as shown below.

$$\text{Lactic acid} + \text{Phenazine Methosulfate (oxidised form)} \xrightarrow[+ \text{NAD}]{\text{Lactate Dehydrogenase}} \text{Pyruvic Acid} + \text{Phenazine Methosulfate (reduced form)} \quad (3)$$

In the chemical process governed by the chemical formula (3) mentioned above, phenazine methosulfate now comes to act as the electron mediator or more specifically, the electron acceptor due to the presence of NAD. Hence, the concentration of lactic acid in the chemical system mentioned above can be obtained by the direct electrochemical measurement of the resultant concentration of phenazine methosulfate of reduced form which is produced.

As may be clear from the description hereinabove, several kinds of attempts for connecting the enzymatic reaction with the electrochemical reaction system have been proposed. Within these attempts, special reference is directed to the conventional arts discussed below concerning the enzyme electrodes which are constituted by immobilizing oxidoreductase.

For example, U.S. Pat. No. 3,542,662 discloses an enzyme electrode comprising an immobilized enzyme membrane composed of a polyacrylicamid gel having GOX therein and covering over an oxygen permeable membrane constituting a polaragraphic oxygen electrode.

The measuring method associated with the electrode mentioned above specifies the method corresponding to that of the substrate concentration being obtained through the electrochemical measurements of the concentration of $O_2$ which reacts with glucose in the presence of the GOX as a catalyst as described in the foregoing.

This arrangement, however, is not reliable to obtain a stable measurement, depending upon the fact that the measuring concentration of $O_2$ itself is quite influenced by the dissolved oxygen concentration in the surroundings of the electrode concerned. Furthermore, the response time concerning the measurement tends to be delayed due to the fact that oxygen must diffuse through two membranes of the immobilized enzyme membrane and the oxygen permeable membrane before it reaches the electrode.

U.S. Pat. No. 3,838,033 discloses an enzyme electrode, in which the outside of the electron collector is covered by a semi-permeable membrane and yet, an enzyme (GOX) and redox compound are both contained in a space provided between the semi-permeable membrane and the electron collector. Furthermore, the redox compound mentioned above is contained in large excess while being present in a partially undissolved form.

The measuring method associated with the electrode mentioned above specifies the method corresponding to that of the substrate concentration obtained by the electrochemical measurement of the redox compound in the system as specifically described in the foregoing. Differing from the measuring situation concerning the oxygen concentration mentioned above in conjunction with the description of U.S. Pat. No. 3,542,662, the concentration of the redox compound remains constant, and thereby, the stable measurment is obtainable.

However, the semi-permeable membrane mentioned above is characterized in that although such a large molecule as the enzyme is not permeated, a small molecule like the substrate is freely permeated therethrough. Therefore, the redox compound whose size is almost equivalent to that of the substrate mentioned above, can be naturally permeated and thereby, gradually lost from the space mentioned above through said membrane.

A portion of the redox compound lost in a manner mentioned above can be supplemented to some extent by the dissolving of the redox compound having been maintained in the undissolved form. However, since the supplement of the redox compound mentioned above can be brought about within limit, the electrode life time does not depend upon the life time of the enzyme, but rather upon the diffusing behavior of the redox compound from the space mentioned above. The characteristic behavior mentioned above also leads to a disadvantage that the electrode life time is quite short.

Moreover, even if the microelectrode comprising the arrangements mentioned above is made to apply for the direct in-vivo measurements, it is not practically possible to utilize the electrode of this type in consideration of the adverse effect caused by the diffusional flow of the redox compounds into the living body.

In Bulletin of the Chem. Soc. of Japan 48(11), 3246, 1975, an electrode comprising an electron collector with which a collagen membrane including therein lactate dehydrogenase or alcohol dehydrogenase in their immobilized condition is brought into close contact, and its measuring characteristics of the substrate concentrations concerning lactic acid and ethanol are disclosed.

However, for every run of the measurement with the electrode mentioned above, the coenzyme (NAD for this case) as well as the redox compound (phenazine methosulfate for this case) which are substantially necessary for the measurements due to the reasons mentioned in the foregoing must be dissolved in the solution containing the substrate to be measured. Accordingly, every measuring run requires these expensive reagents without any possibility of reusing them. Moreover, the procedures used to prepare the predetermined fixed amount of the redox compound as well as that of the coenzyme for every run of the measurement will involve additional complexities for the measuring operation. As the matter of fact, the electrode of the above described type can not be applicable to the in-vivo concentration measurements due to the inherent defects mentioned in the foregoing.

As is clear from the description in the foregoing, the conventional enzyme electrodes comprising immobilized oxidoreductase still involves substantial defects and thereby, their applications are quite limited.

SUMMARY OF THE INVENTION

Accordingly, an essential object of the present invention is to provide an enzyme electrode to be incorporated either in a substrate measuring system or in an electric current producing cell or to be utilized for synthesizing processes in which an oxidoreductase as well as a redox compound acting as an electron mediator in an enzymatic reaction are both maintained in immobilized states thereof on or in the neighborhood of the electron collector.

Another important object of the present invention is to provide an enzyme electrode of the above described type in which, as in the case where the enzymatic reaction specifically requires the presence of a coenzyme as the electron mediator in cooperation with the redox compound, the coenzyme is further maintained in an immobilized state thereof on or in the neighborhood of the electron collector used.

A further object of the present invention is to provide an enzyme electrode of the above described type which can be formed on a small scale to be employed for in-vivo concentration measurements therewith.

In accomplishing these and other objects according to one preferred embodiment of the present invention, there is provided an enzyme electrode, which comprises an electrode holder of an electrically insulating material, an electron collector of a platinum formed in a disc-like configuration and attached to a recess provided in a bottom end of the holder mentioned above, a semi-permeable membrane made from cellophane or collodion and enclosing a whole bottom face and its extending longitudinal, peripheral surface of the holder mentioned above, a leading wire connected with the electron collector mentioned above, and a space which is provided between the electron collector and the semi-permeable membrane. More specifically, the space mentioned above is a provision for entrapping the redox polymer and the enzyme therein.

Since the redox compound of the present invention is in the form of polymer, the redox polymer and glucose oxidase dissolved in the phosphoric acid buffer solution and entrapped in the space with the membrane never diffuses out of the electrode membrane.

As may be clear from the arrangements described in the foregoing, oxidoreductase (glucose oxidase for this embodiment) and a redox polymer are both in an immobilized state in the neighborhood of the electron collector.

In the following embodiment, there is described an enzyme electrode in which the enzyme (alcohol dehydrogenase) and the redox polymer (a compound of a hydroxymethulated polyacrylicamide with an attached riboflavin-5'-phosphate ester), and further, a coenzyme (nicotinamide adenine dinucleotide NAD) are all brought into an immobilized state to constitute the electrode.

Firstly, the coenzyme (NAD) is reacted with sepharose which is specified as a polysaccharide carrier so as to be brought into an immobilized state by the covalent bond therebetween.

Subsequently, the enzyme electrode is constituted by a series of steps of mixing the immobilized NAD and the redox polymer mentioned above with graphite powder (the electron collector for this embodiment), moulding the resultant mixture with a press, and successively cross-linking alcohol dehydrogenase onto the surface of the resultant mould by glutaldehyde, so that alcohol dehydrogenase is maintained in an immobilized state.

As may be clear from the description concerning the embodiment mentioned above, the enzyme, coenzyme and redox compound are all in immobilized states on and in the neighborhood of the electron collector.

In another other embodiment in which gallocyanine is employed as the redox compound, the redox compound is chemically brought into an immobilized state on the electron collector by being chemically bonded thereto.

BRIEF DESCRIPTION OF THE DRAWINGS

These and other objects and features of the present invention will become apparent from the following description taken in conjunction with the preferred embodiment thereof with reference to the accompanying drawings, in which.

Before the description of the present invention proceeds, it is to be noted that like parts are designated by like reference numerals through several views of the accompanying drawings.

DETAILED DESCRIPTION OF THE INVENTION

For a detailed understanding of the invention, reference is made to the subsequent description of various embodiments thereof.

First of all, as for a method for making the redox compound to be used in an immobilized state, various embodiments in which macromolecular compounds containing redox compounds are to be combined with the immobilized enzyme, will be detailed hereinbelow.

The macromolecular compounds which contain the redox compounds mentioned above are often simply called by a name of either a redox polymer or a redox resin.

EXAMPLE 1

In the following embodiment of the present invention, as for the enzyme and the redox compound, GOX and a condensation polymer composed of p-benzoquionone, formaldehyde and piperazine hydrochloride and having the following structural formula were employed.

Figure 1:
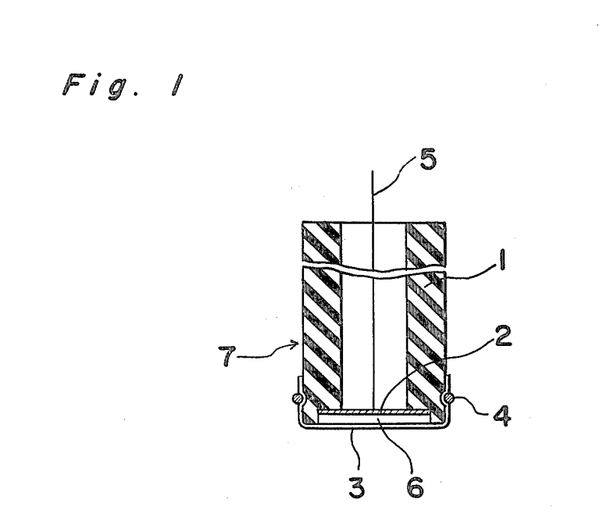
FIG. 1 is a schematic diagram partially showing a sectional side view of an enzyme electrode according to the present invention.

Referring now to the drawings, FIG. 1 specifically shows structural details of the enzyme electrode of the present invention. From a structural viewpoint, the enzyme electrode of the present invention comprises a cylindrical electrode holder 1 of an electrically insulating material, an electron collector 2 of a platinum formed in a disc-like configuration and attached to the recess provided in a bottom end of a cylindrical electrode holder 1 mentioned above, a semi-permeable membrane 3 made from cellophane or collodion and enclosing the whole bottom face and the extending longitudinal, peripheral surface of the cylindrical electrode holder 1 mentioned above, a ring 4 for fixing therewith the membrane 3 mentioned above to the outer peripheral surface of the holder 1, a leading wire 5 connected with the electron collector 2 mentioned above, and a space 6 which is provided between the electron collector 2 and the semi-permeable membrane 3 and positioned below the partial bottom surface of the holder 1.

More specifically, the space 6 mentioned above is a provision for entrapping the redox polymer and the enzyme therein.

Since the redox polymer of this embodiment exhibit water soluble characteristics, the redox polymer mentioned above and GOX are both dissolved in a phosphoric acid buffer solution having a pH of 5.6 and thereby, the resultant solution is entrapped in the space 6 with the membrane 3.

In the arrangements mentioned above, since the respective molecules of the enzyme and the redox polymer are both relatively large, these molecules entrapped in the space 6 cannot be permeated through the membrane mentioned above and thereby, being immobilized in the space 6, and more particularly, in the neighborhood of the electron collector 2.

The fundamental difference between the present enzyme electrode mentioned above and that shown in U.S. Pat. No. 3,838,033 mentioned earlier is that the redox compound of the present invention is in the form of a polymer. Therefore, the redox compound of the present invention does never diffuses out of the electroae membrane.

Figure 2:
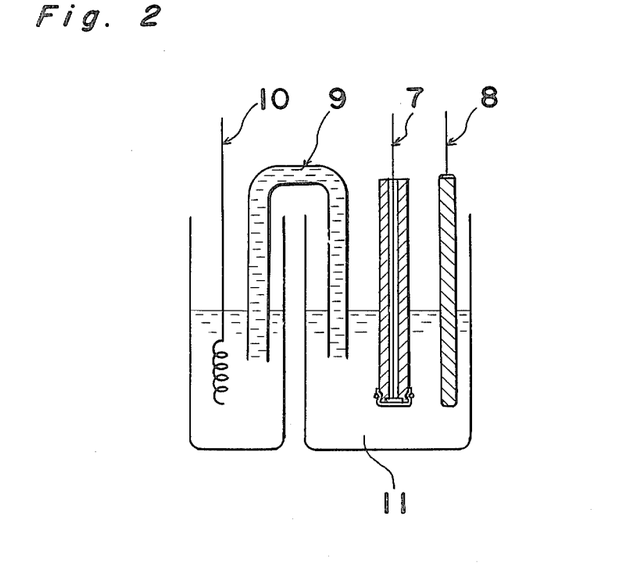
FIG. 2 is a schematic diagram showing a sectional side view of a substrate measuring system incorporated in one of the embodiments of the enzyme electrodes according to the present invention.

Referring now to FIG. 2, an embodiment of a measuring system incorporated by the enzyme electrode 7 of the present invention is illustrated.

With the measuring system mentioned above, the measurements of the change of the anodic current, that is, the oxidation current of the reduced redox polymer were made on glucose solutions ranging in concentrations of from 0 to $3 \times 10^{-3}$ mol/l under experimental conditions such taht the electrode 7 is kept under constant potential with reference to a saturated calomel electrode 8 (S.C.E.) (i.e., +0.4 V vs. S.C.E.).

In FIG. 2, the successive reference numerals from 9 to 11 indicate a salt bridge 9, a counter electrode 10, and buffer solution 11 containing the substrate therein, respectively.

Figure 3:
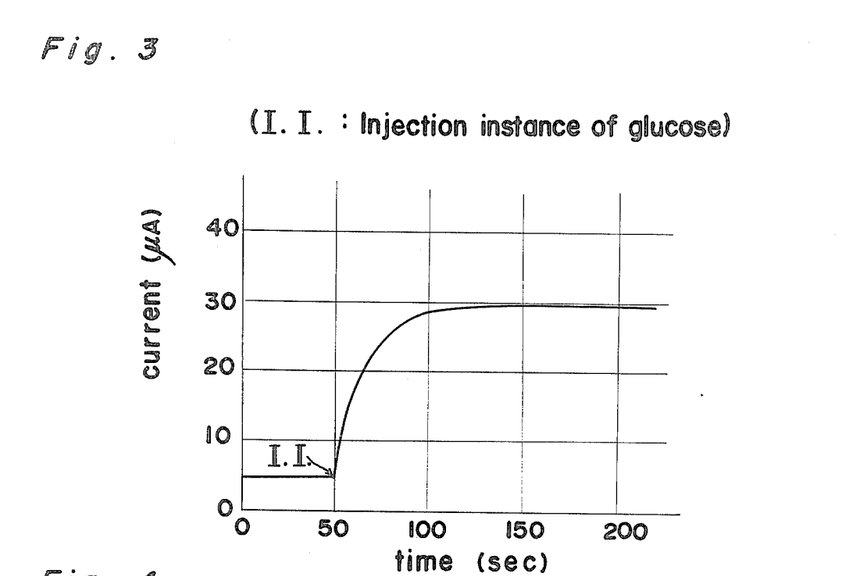
FIG. 3 is a graph showing a current response curve concerning a specific glucose concentration with the enzyme electrode shown in FIG. 1.

Referring now to FIG. 3, there is schematically shown a current response curve (a variation of the current caused by the concentration changes of glucose with respect to time). As is clear from this figure, the current caused by the certain specific glucose concentration in the measuring system mentioned above comes to a certain steady value of 30 μA, being increased by 25 μA, within two minutes from the instance that a specific amount of glucose is added to the measuring system.

Figure 4:
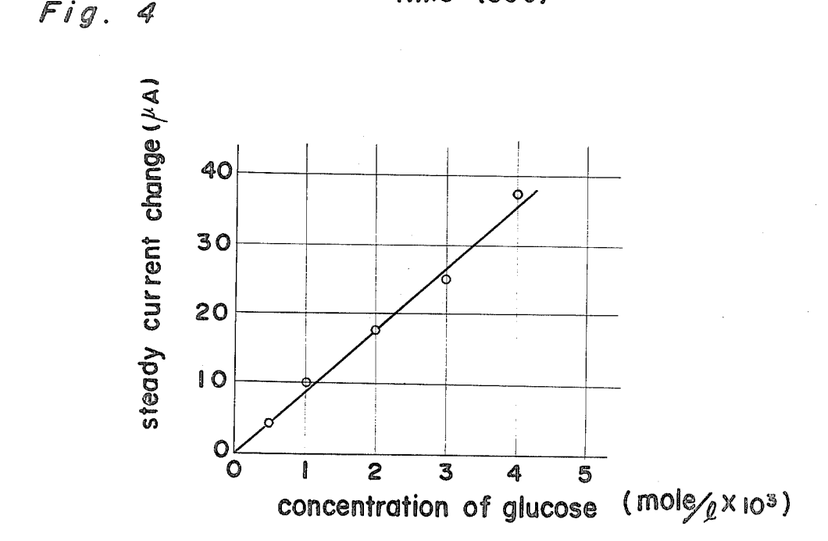
FIG. 4 is a graph showing a resultant linear relation correlating a concentration of glucose with the steady current value.

Referring now to FIG. 4, this figure illustrates the change of a steady current-glucose concentration relationship, the change of the steady currents being plotted against the various glucose concentrations.

As is clear from FIG. 4, within the range of a glucose concentration of $0.5 \times 10^{-3}$ to $4 \times 10^{-3}$ mol/l, the relation between the concentration and its steady, prevailing value of current gives a linear relationship, which relationship confirms the possibility of determining the glucose concentration with the enzyme electrode of the present invention. The above described enzyme electrode of the present invention was maintained in a normal measurable condition thereof as long as for about two months without causing any measuring defects, as the electrode mentioned was stored in buffer solution.

Futhermore, the enzyme, which is simply dissolved in a buffer solution to prevent the diffusion thereof out of the semi-permeable membrane in the embodiment mentioned in the foregoing, can be alternatively converted into an immobilized condition thereof either by an entrapping method using a polyacrylicamide gel or by a cross-linking method using glutaldehyde.

An enzyme electrode comprising an enzyme in an immobilized condition by using by glutaldehyde is effected by using the glutaldehyde in a dispersed condition in a solution contained in the space 6 mentioned above. Such enzyme electrode showed an increase in current of about 20 μA for a glucose concentration of $3 \times 10^{-3}$ mol/l and yet, it took about three minutes before the steady current value mentioned above was achieved.

The enzyme electrode mentioned above exhibited normal measurable conditions for the measuring glucose concentration for as long as about four months.

The enzyme immobilized with glutaldehyde is capable not only being dispersed in buffer solution, but also of directly fixing onto the surface of the semi-permeable membrane 3 shown in FIG. 1. The latter method for immobilization did not show any substantial differences in electrode characteristics even when compared with the former method previously mentioned.

EXAMPLE 2

As for using a enzyme and a redox polymer, GOX and a compound composed of a hydroxymethylated polyacrylicamide with attached p-benzoquinone and having the following structural formula such materials were respectively employed in this embodiment.

Since the polymer of this embodiment is water-insoluble, the fine powder of this polymer was mixed with both GOX and an electron collector such as carbon powder, and then the resultant mixture, was further mixed with a buffer solution to bring it into a gel-like state. An enzyme electrode was then assembled in a manner such that the gel-like substance was entrapped in the space 6 as shown in FIG. 1.

As might be clear from the arrangements concerning the enzyme electrodes mentioned above, each of the enzyme, redox compound and electron collector are mixed and in contact with each other, and maintained in an immobilized state thereof in the neighborhood of the second electron collector made of a platinum plate.

With the enzyme electrode of the above described type, the current response tests concerning the current vs. the specific glucose concentration were carried out under the same experimental conditions, as that of Example 1.

The experimental results showed that the increase in the current for a specific glucose concentration of $3 \times 10^{-3}$ mol/l was about 30 μA, while it took about a minute before the current mentioned above to reach a steady value.

The enzyme electrode of the above described type was maintained in a normal measurable state for as long as a month.

Furthermore, when a water-insoluble redox condensation polymer composed of p-benzoquinone and formaldehyde and having the structual formula shown below was employed as for the redox compound, the same current-substrate concentration characteristics were acknowledged.

EXAMPLE 3

As for the enzyme and the redox polymer, GOX cross-linked by glutaldehyde, and a compound composed of hydroxymethylated polyacrylicamide attached by thionine and having the following structural formula were respectively employed. The compound mentioned above is further water-insoluble.

These enzyme and redox polymer were moulded by a press and forced into contact with the electron collector of platinum after the successive steps of the mixing with a carbon powder, and a binder of a fluorocarbon polymer powder.

The enzyme electrode thus-arranged in a manner as mentioned in the foregoing, substantially permits the composite substance of enzyme and redox compound, including the electron collector (carbon) to be maintained in an immobilized state in the neighborhood of the second electron collector (platinum) concerned.

In the experimental conditions wherein the electrode is kept under a constant potential of +0.2 V with reference to the saturated calomel electrode, measurements of the changes of current caused by the changes of substrate concentrations were carried out.

The experimental results showed that an increase in the current for a specific glucose concentration of $3 \times 10^{-3}$ mol/l was about 20 $\mu$A, while it took a minute before the current reached a steady value.

EXAMPLE 4

As for the redox polymer, a hydromethylated styreneacrylicamide copolymer with attached p-benzoquinone and having the following structual formula was used in this embodiment.

The enzyme electrode of this embodiment is made through the successive steps of coating and successively drying a tetrahydrofuran solution of the compound mentiond above onto the surface of the electron collector of platinum and further, directly immobilizing GOX by glutaldehyde on the surface mentioned above which has been already treated in the previously described manner.

The redox polymer of the present invention is soluble in tetrahydrofuran, but is insoluble in buffer solution.

Figure 5:
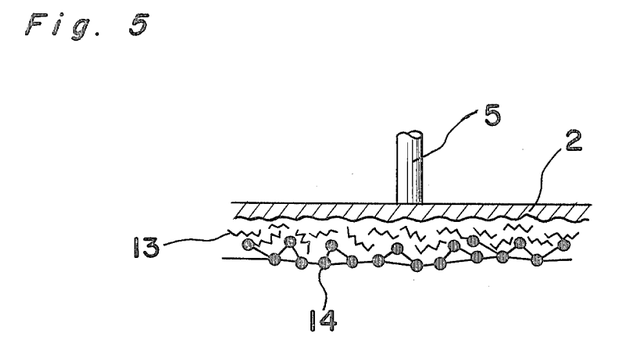
FIG. 5 is a fragmentary side view, in section, on a greatly enlarged scale, of another modification of an enzyme electrode according to the present invention.

Therefore, since the composite substance of the enzyme and the redox compound is maintained in an immobilized condition thereof on the electron collector, the provision of a semi-permeable membrane is not especially necessary for maintaining the enzyme and the redox compound around the collector, which situation, however, has been already, likewise brought about by the embodiment described in the Example 3. The structural detailed and features of the electrode mentioned above is shown in FIG. 5, in which the reference numerals 13 to 14 successively indicate, a redox polymer coated onto the surface of the electron collector 2, and a cross-linked enzyme molecule 14, respectively.

The functional characteristics of the enzyme electrode of the present embodiment are as follows.

The increase in the current for the specific glucose concentration of $3 \times 10^{-3}$ mol/l was about 40 $\mu$A, while it took about a minute before the current mentioned above reached a steady value. This electrode was maintained in a normal measurable condition for the glucose concentration measurements for about two months.

EXAMPLE 5

As for the redox polymer, an ion-exchange resin, and more specifically, a cation-exchange resin (which is commercially available in a name of Amberlite IR-120) containing potassium ferricyanide through an absorption process, was employd in this embodiment.

The redox polymer mentioned above was further mixed with carbon powder, GOX cross-linked by glutaldehyde and a fluorocarbon polymer powder, and then, this mixture was fixed onto the electron collector of platinum by a moulding step through a press-work, whereby the electrode of this embodiment was produced.

The electrode mentioned above showed an increase in the current of about 15 $\mu$A for a specific glucose concentration of $3 \times 10^{-3}$ mol/l, while it took about a minute before the current mentioned reached a constant or steady value.

Furthermore, the alternative employment of the following iron salt of a polyacrylic acid having the structual formula shown below as for the redox polymer in this embodiment, showed approximately the same experimental results mentioned in the foregoing.

EXAMPLE 6

An enzyme electrode similar to that as described in the Example 3, was employed except that cholesterol oxidase was employed as the enzyme. This enzyme electrode showed an increase in current of about 2 $\mu$A for a specific cholesterol concentration of $1 \times 10^{-3}$ mol/l, while it took about two minutes before the current mentioned reached a steady value thereof. This enzyme electrode was maintained in a normal condition for measuring the cholesterol concentration for as long as about a month.

EXAMPLE 7

An enzyme electrode slmilar to that as described in Example 2, was used except that xanthine oxidase was employed as the enzyme. This enzyme electrode showed an increase in current of about 10 $\mu$A for the specific xanthine concentration of $1 \times 10^{-3}$ mol/l, while it took about two minutes before the current mentioned above reached a constant or steady value.

Furthermore, this electrode was maintained in a normal condition for measurements of xanthine concentration as long as for a month.

In the following embodiment, the redox compound is chemically brought into an immobilized state on the electron collector by chemical bonding.

EXAMPLE 8

Gallocyanine having a structual formula described below was employed for the redox compound in this embodiment.

The enzyme electrode of the present embodiment was made by the successive steps of immobilizing gallocyanine onto an electron collector of tin oxide ($SnO_2$ nesa-glass) through the ester bond caused by the surface hydroxyl groups thereof, and subsequently, further chemically superimposing GOX which is to be immobilized by glutaldehyde.

The $SnO_2$ electrode mentioned above, in which the redox compound and the enzyme of respective immobilized states surround the electron collector in succession, showed an increase in current of 0.1 $\mu A$ for a specific glucose concentration of $3 \times 10^{-3}$ mol/l, while it took about two minutes before the current mentioned above reached a steady value.

EXAMPLE 9

In this embodiment the redox compound is chemically brought into an immobilized state on the electron collector through either the bond caused by the reaction of a carboxyl group existing on the surface of the electron collector of carbon with indophenol whose structual formula is shown below, and furthermore, on the chemically treated surface mentioned above, an aldehyde oxidase (the enzyme of the present embodiment) was further chemically fixed by means of glutalaldehyde due to its cross-linked effects previously described.

The enzyme electrode thus-made showed an increase in current of 0.5 $\mu A$ for a specific acetaldehyde concentration of $1 \times 10^{-3}$ mol/l, while it took about two minutes before the current reached a steady value.

In the following description, an enzyme electrode, in which an enzyme and a redox compound, and further, a coenzyme are all brought into immobilized states thereof, to constitute an enzyme electrode, are detailed.

EXAMPLE 10

As for the coenzyme, nicotinamide adenine dinucleotide (NAD) was employed in this embodiment. The coenzyme (NAD) was reacted with sepharose which is specified as a polysaccharide carrier so as to be brought into an immobilized state by the covalent bond therebetween. As for the redox polymer, a compound of a hydroxymethylated polyacrylicamide with an attached riboflavin-5'- phosphate ester was employed, and the structural formula of the compound is illustrated below.

The enzyme electrode of this embodiment is made by a series of steps of mixing the immobilized NAD and the redox polymer with graphite powder, moulding the resultant mixture with a press, and successively making alcohol dehydrogenase to be cross-linked onto the surface of the resultant moulds by glutaldehyde, so that alcohol dehydrogenase is maintained in an immobilized state.

With the electrode comprising the immobilized constituents of the enzyme, the redox compound and the coenzyme, the response tests concerning the substrate concentration were carried out under experimental conditions such that the electrode is kept under a constant potential of +0.1 V with reference to the saturated calomel electrode. The experimental results showed an increase in current of about 20 $\mu A$ for a specific ethanol concentration of $1 \times 10^{-3}$ mol/l, while it took about three minutes before the current reached a steady value.

EXAMPLE 11

The electrode of this embodiment was made by a series of steps of adding a phosphoric acid buffer solution containing a coenzyme NAD and lactote dehydrogenase in a dissolved state and being of a pH of 7.7, to a powder mixture of graphite powder and a redox polymer as employed in Example 10, drying the resultant mixture to convert it into a powder mixture, making the coenzyme and enzyme of this embodiment to be simultaneously cross-linked onto the powder mixture of graphite and redox polymer by glutaldehyde, so that the coenzyme and enzyme are both maintained in an immobilized state. Subsequently, the resultant mixture described above is moulded by a press, so that the respective immobilized enzyme, coenzyme, and redox compound and the electron collector are altogether composed as a unit, to make the resultant electrode of the present embodiment.

This resultant electrode showed an increase in a current of about 15 $\mu A$ for a specific lactic acid concentration of $1 \times 10^{-3}$ mol/l under the same experimental conditions described in Example 10.

Although such materials as platinum, carbon, including graphite, and tin oxide are used for the material of the electron collector in the embodiments mentioned in the foregoing, other materials such as noble metals including gold, silver, iridium, palladium, etc. and their alloys, may be used. Also corrosion-resistant metals including titanium, tantalum etc., and their alloys, can be used electrical conductive oxides including ruthenium oxide, etc., can be used semiconductor materials including silicon, germanium, titanium oxide etc., can be employed as an electron conductor material.

Furthermore, as for the method for immobilizing the enzyme, although the method of preventing occurrence of the diffusional flow of the enzyme with a semipermeable membrane, may be used the entrapping method by use of polyacrylicamide and a cross-linking method by use of gultaldehyde can also be employed. Further it is possible to immobilize the enzyme by attaching the enzyme onto a water-insoluble carrier by a covalent linkage.

Moreover, although a number of redox polymers are described in the foregoing, it is possible that these polymers may not have the proper chemical structures of the polymers shown in the chemical structural formulas illustrated in the foregoing, wherein, for example, not only cross-linking between the polymer chains, but also the release of the redox compound from the polymer chains may be included.

As is clear from the description in the foregoing, this invention specifically provides a novel electrode using a redox compound acting as an electron mediator of oxidoreductase, an enzyme and, where necessary, including a coenzyme to be maintained in an immobilized state thereof onto or in the neighborhood of the electron collector, and furthermore, the applicability of the present invention is not limited to these of the redox derivatives, nor the arrangements for the surface modification of the electron collector, nor the methods for immobilizing enzymes or coenzymes as described in the foregoing.

More specifically, at least two kinds of each of the enzymes, redox compounds, and coenzymes may be employed and they can be employed by the combination with one of the other kinds mentioned in the foregoing, and yet, as far as the immobilizing method concerned, various methods can be combined with each other for accomplishing the immobilization of the constituents of the electrode mentioned above.

As far as the enzyme is concerned, a multienzyme reaction system, which comprises the consecutive steps of; firstly immobilizing the enzyme belonging to the nonoxidoreductase in the presence of a oxidoreductase, and successively converting the substrate associated with the former enzyme into the substrate which is to be associated with the latter enzyme through the enzymatic reaction concerning the former enzyme, can be used. Furthermore, as for the enzyme, in addition to the naturally extracted substances, those substances which have been chemically modified to promote their activities can be employed.

Still furthermore, a microorganism and orgarelle including the enzyme can be brought into the immobilized condition and thereby, made a constituent of the electrode without said enzyme being isolated from the microorganism or organelle mentioned above.

As the arrangements of the present invention do not permit either one of the enzymes, redox compounds, and coenzymes to be diffused into solution to be measured, the present electrode can be reused, with its accuracy in functioning being maintained. When these enzyme electrode, references electrode and counter electrode are incorporated with each other to compactly constitute an electrode, this resultant miniature electrodes can offer the possibility of handy, direct in-vivo substrate concentration measurements within a short period of time without adding foreign substances to the body fluid.

The utilization of the enzyme electrode of the present invention is not limited to an electrode to measure substrate concentrations, but can be used as an electrode constituting an electric current producing cell. For example, the enzyme electrode composed of an immobilized combination of glucose oxidase and thionine described in the Example 3, with the counter electrode of the oxygen electrode can provide a glucose fuel cell.

The structual characteristics of the glucose fuel cell mentioned above are shown in FIG. 6, wherein the respective reference numerals 16 to 21 indicate in succession, the enzyme electrode 16, the oxygen electrode 17, a separator 18, an electrolyte solution such as phosphoric acid buffer solution 19, a gas chamber 20 to which oxygen or air is supplied, a fuel chamber 21 to which glucose solution is supplied as a fuel.

Figure 6:
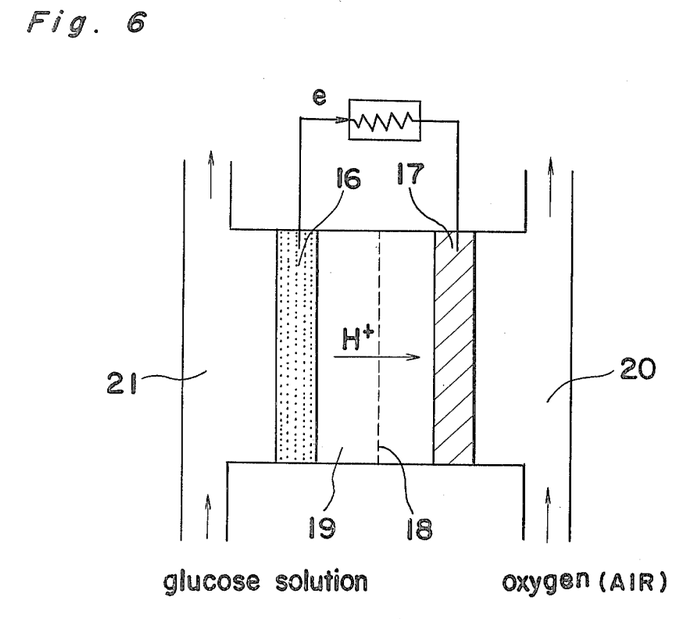
FIG. 6 is a schematic diagram showing an electrical cell incorporated by one of the enzyme electodes according to the present invention.

This fuel cell arranged in the aforementioned generates an electric potential of about 0.7 volt, and the specific value is electric current of about 1 mA was. In the arrangements concerning the fuel cell mentioned above, the redox compound itself is maintained in an immobilized condition in this specific cell, as may be clear from the description in the Example 3, and thus, did not need any redox compound supplement. Therefore, the arrangements of the fuel cell mentioned above specifies the cell of fuel supplemented type in the best sense of the term, and effectively functioned as a cell as long as for about six months.

As for the further utilization of the enzyme electrode of the present invention, this electrode can be available for a process of synthesizing, for example, gluconic acid, which is obtained by the spontaneous hydrolysis of gluconolactone through the chemical treaties concerning glucose, or pyrubic acid through the chemical treaties concerning lactic acid.

Moreover, as for the further advantages associated with the utilization of the electrode of the above mentioned type, in the synthesizing processes mentioned above, as the respective products do not include such the foreign substances as enzymes, or redox compounds or coenzymes therein, the isolation of the substance to be synthesized is quite simplified.

Although the present invention has been fully described by way of example with reference to the accompanying drawings, it is to be noted that various changes and modifications are apparent to those skilled in the art. Therefore, unless otherwise such changes and modifications depart from the scope of the present invention, they should be construed as included therein.

What is claimed is:

1. An enzyme electrode which at least comprises an oxidoreductase enzyme, an artificial redox compound acting as an electron mediator in an enzymatic reaction associated with said oxidoreductase, said redox compound being selected from the group consisting of p-benzoquinone, methylene blue, 2,6-dichloropholindophenol, potassium ferricyanide, thionine, gallocyanine, indophenol and a riboflavin -5'-phosphate ester, and an electron collector, said oxidoreductase enzyme and said redox compound being in an immobilized state in juxtaposition or in contact with said electron collector.

2. An enzyme electrode as claimed in claim 1, which further includes a coenzyme for acting as said electron mediator in co-operation with said redox compound, wherein said coenzyme is in an immobilized state in juxtaposition on or in contact with said electron collector.

3. An enzyme electrode as claimed in claim 2, wherein said redox compound is in the form of a polymer.

4. An enzyme electrode as claimed in claim 2, wherein said redox compound is immobilized by being affixed to the electron collector by covalent chemical bonds as a result of a chemical reaction between the electron collector and the redox compound.

5. An enzyme electrode as claimed in claim 1, wherein said redox compound is in the form of a polymer.

6. An enzyme electrode as claimed in claim 1, wherein said redox compound is immobilized by being affixed to the electron collector by covalent chemical bonds as a result of a chemical reaction between the electron collector and the redox compound.

7. An enzyme electrode according to claim 1, which comprises a cylindrical electrode holder made of an electrically insulating material containing a recess provided in the bottom end of the holder; an electron collector 2 in a disc-like configuration located in the recess provided at the bottom end of said holder; a semi-permeable membrane covering and enclosing the whole bottom face of the extending longitudinal peripheral surface of the electrode holder so as to provide a space between the electron collector and the membrane; a ring for affixing the membrane to the outer peripheral surface of the holder 1 and a leading wire in contact with the electron collector and extending outward from the top of the electrode holder; wherein the oxidoreductase enzyme and the redox compound are in an immobilized state in the space between the electron collector and the membrane covering the bottom of the cylindrical electrode holder.

8. An enzyme electrode according to claim 7, wherein the electron collector is made out of platinum and the semi-permeable membrane is made out of a material selected from the group consisting of cellophane and collodion.

9. An enzyme electrode according to claim 8, wherein the redox compound is in the form of a polymer, and wherein the polymeric redox compound and oxidoreductase material are each of such molecular size as to be incapable of permeating through the semi-permeable membrane, thereby being immobilized within.

10. An enzyme electrode according to claim 7, wherein the redox compound is immobilized by being affixed onto the electron collector by covalent chemical bonds as a result of a chemical reaction between the redox compound and the electron collector.

* * * * *